May 23, 1972 W. H. JESSEL, JR., ET AL Plant Pat. 3,184
CHRYSANTHEMUM PLANT
Filed July 27, 1970
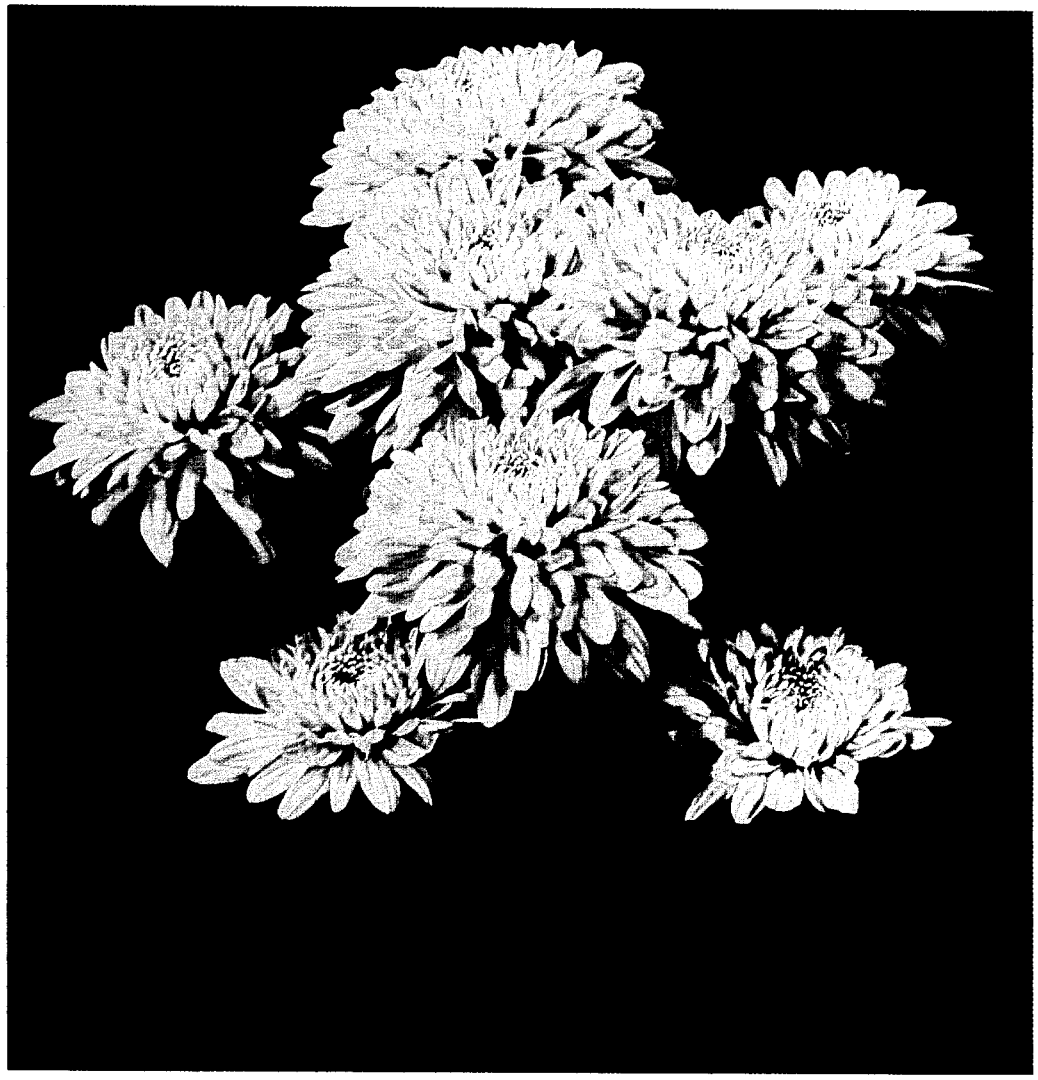
INVENTORS
WALTER A. JESSEL, JR.,
WILLIAM E. DUFFETT
BY
Oberlin, Maky, Donnelly & Renner
ATTORNEYS United States Patent Office Plant Pat. 3,184
Patented May 23, 1972

3,184
CHRYSANTHEMUM PLANT

Walter H. Jessel, Jr., Doylestown, and William E. Duffett, Akron, Ohio, assignors to Yoder Brothers, Inc., Barberton, Ohio Filed July 27, 1970, Ser. No. 58,750
Int. Cl. A01h 5/00
U.S. Cl. Plt.—80 1 Claim The present invention comprises a new and distinct variety of pompon chrysanthemum plant which is a sport of a light pink seedling identified for breeding purposes as YB 63340–1.

The new variety is similar in many respects to Bluechip, an unpatented but well-known commercial variety of Yoder Brothers, Inc., Barberton, Ohio. Both varieties have the same characteristics of:

(1) Vigor.
(2) Nine week response.
(3) Upper foliage color.

The new variety is distinguished from Bluechip by the following chracteristics, with the comparison being based on growth under identical culture and conditions:

(1) A truer pink color with less lavender tones.
(2) Flowers ¼" larger.
(3) Increased flower production per stem. Twenty to twenty-five percent more of the stems will produce 5–7 or more flowers per spray than Bluechip.
(4) More flowers produced from laterals down the stem, rather than on a similar plane at the top of the spray, like Bluechip.
(5) A more open spray formation than Bluechip.
(6) Produces more shoots or breaks from a pinch, averaging 2–3 more shoots per plant than Bluechip. This trait is particularly prevalent during high temperature periods.
(7) Average fresh weight per stem is 15%–20% heavier than Bluechip.
(8) Foliage less serrated than Bluechip.
(9) A more uniform response in all periods, combined with an earlier response of approximately 5–7 days in summer and early fall (high temperature periods) than Bluechip.

The new variety was discovered upon examination of a flowering block of the parent variety.

My new variety has been asexually reproduced by cuttings at Barberton, Ohio, and has been found to retain its distinctive characteristics through successive propagations.

My new variety when grown in the vicinity of Salinas, Calif.; Fort Myers, Fla. and Barberton, Ohio has a response period of approximately 9 weeks. It will be understood that the response time and blooming period may vary significantly with varying environmental conditions such as temperature, light intensity and day length. Suggested flowering in northern United States is from April through November, and for southern Florida, from December through April.

The following detailed response data is based on observations made of the new variety in a greenhouse in Barberton, Ohio. Normal response of the new variety is approximately 9 weeks, accelerating to 8½ weeks under spring conditions and slowing to 9½ weeks in mid-summer and early fall under high temperature conditions. By way of contrast, Bluechip will respond normally in 9½ weeks and will accelerate its response to 8½ weeks under spring conditions. However, the response of Bluechip will slow to 10 weeks under summer and fall high temperature conditions.

The accompanying drawing shows the color and form of my new variety, with the color being as true as possible with color illustrations of this type.

The following is a detailed description of my new variety, with the color references being to the Munsell Color Chart, 1963 Edition, and comparisons made in certain instances with the cultivar Bluechip.

Botanical classification: *Chrysanthemum morifolium.*

| | Belair | Bluechip |
|---|---|---|
| Bloom: | | |
| Size | 2¾". | 2½". |
| Fully expanded | 3¼". | 3". |
| Borne | Terminal cluster of 8–12 on elongated pedicel, according to culture. | 3". |
| Stems | Elongated pedicels 6"–10" in length branching from main stem. | 3". |
| Form | Decorative | 3". |
| Permanence | 7–10 days | 3". |
| Color: | | |
| Center of flower. | Pink, 2.5RP7/6 | Lavender, 10P7/6 |
| Base of petals | Pink, 10P8/6 | Do. |
| Inside of petals. | Light pink, 10P8/6 | Do. |
| Reverse of petals. | Light pink, 2.5RP8/2 | Grey lavender, 10P8/4 |
| Tonality from a distance | Pink | Lavender. |
| Discoloration | Pale pink, 5RP8/5 | Grey lavender, 10P8/4 |

*Petals.* — Texture — smooth; appearance—slightly open at base, keeled at mid-point, tapering to a blunt point; arrangement—composite whorled on a single receptacle; persistence—shatter resistant; fragrance—typical chrysanthemum.

*Reproductive organs.*—Stamen, anthers—none to 20, depending on culture; pollen—none to scant; arrangement—center of flower if present; styles—present in both ray and disc floret; length—short; ovaries—at base of petals attached to receptacle.

*Plant.* — Form — herbaceous; growth — upright; height—36" to 42" depending on culture.

| | Belair | Bluechip |
|---|---|---|
| Foliage: | | |
| Top side | Green, 7.5GY3/4 | Green, 7.5GY3/4. |
| Size | 7"–9" long including petiole 4"–5" wide. | 6½"–3½" long including petiole 4"–5" wide. |
| Quantity | Numerous | Numerous. |
| Shape | Palmate | Palmate. |
| Texture | Coarse | Coarse. |
| Ribs and veins | Prominent | Prominent. |
| Edge | Deeply indented | Deeply indented. |
| Serration | Slight | Very slight. |
| Underside | Light green, 5GY4/4 | Light green, darker than Belair, 7.5 GY4/4. |
| Stipules | Prominent at base of petiole. | Rudimentary at base of petiole. |

I claim:

1. A new and distinct variety of pompon chrysanthemum characterized particularly as to novelty by a unique pink color, greater flower production per stem, more open terminal sprays, lateral flowering down the stem, excellent breaking action on pinched crops, especially during high temperature periods, and a more uniform response to all periods, with an earlier response during high temperature periods.

No references cited.

ROBERT E. BAGWILL, Primary Examiner

UNITED STATES PATENT OFFICE
CERTIFICATE OF CORRECTION

Patent No. PP 3,184 Dated May 23, 1972

Inventor(s) Walter H. Jessel, Jr. and William E. Duffett

It is certified that error appears in the above-identified patent and that said Letters Patent are hereby corrected as shown below:

In column 2, line 14 opposite Borne; line 15 opposite Stems; line 17 opposite Form and line 18 opposite Permanence delete 3" under Bluechip in each line.

In column 2, approximately line 47, adjacent the heading "Size" and under the cultivar heading "Bluechip", "3-1/2" should read --8-1/2"--.

Signed and sealed this 2nd day of October 1973.

(SEAL)
Attest:

EDWARD M.FLETCHER,JR.
Attesting Officer

RENE D. TEGTMEYER
Acting Commissioner of Patents

USCOMM-DC 60376-P69
☆ U.S. GOVERNMENT PRINTING OFFICE : 1969 O—366-334

Dedication

PP. 3,184.—*Walter H. Jessel, Jr.*, Doylestown, and *William E. Duffett*, Akron, Ohio. CHRYSANTHEMUM PLANT. Patent dated May 23, 1972. Dedication filed Feb. 6, 1975, by the assignee, *Yoder Brothers, Inc.*

Hereby dedicates to the Public the entire remaining term of said patent.

[*Official Gazette July 1, 1975.*]